United States Patent [19]

Zeltner

[11] 4,279,516
[45] Jul. 21, 1981

[54] CONTAINER FOR PASTEURIZING SLUDGE

[75] Inventor: Erich Zeltner, Gockhausen, Switzerland

[73] Assignee: Von Roll AG, Gerlafingen, Switzerland

[21] Appl. No.: 50,493

[22] Filed: Jun. 20, 1979

[30] Foreign Application Priority Data

Jun. 26, 1978 [CH] Switzerland .......................... 6950/78

[51] Int. Cl.$^3$ .............................................. B01F 7/24
[52] U.S. Cl. .................................... 366/171; 366/318; 366/331
[58] Field of Search ............... 366/168, 171, 174, 318, 366/319, 323, 324, 325, 331, 338, 339; 159/2 E

[56] References Cited

U.S. PATENT DOCUMENTS

| 273,084 | 2/1883 | Hoppes | 366/174 X |
| 1,277,145 | 8/1918 | Sowers et al. | 366/168 X |
| 1,968,994 | 8/1934 | Davies | 366/318 X |
| 2,011,055 | 8/1935 | Klugh | 159/2 E X |
| 2,628,827 | 2/1953 | Daman | 366/325 X |
| 3,211,209 | 10/1965 | Latinen et al. | 159/2 E X |
| 3,797,550 | 3/1974 | Latinen | 366/323 X |

Primary Examiner—Philip R. Coe

Attorney, Agent, or Firm—Weingarten, Maxham & Schurgin

[57] ABSTRACT

A vertically standing, slender, cylindrical flow container with an upper intake connection for crushed raw sludge already heated to a pasteurization temperature and a lower outlet connection for pasteurized sludge. A slowly rotating guide member is incorporated into the container coaxially with the longitudinal axis of the latter and is driven by an electric motor via a reduction gear. The tube-like guide member core is provided with a plurality of continuous, helically-wound blades which extend from top to bottom and which, with respect to the direction of rotation of the guide member, form front and rear helical deflectors for the sludge. The helically wound blades also subdivide the circular cross-section of the passage of the container into a plurality of helically-wound individual channels. At the upper end of the container, the guide member is suspended in a combined radial/axial bearing outside the sludge area thereof, and in the lower part of the container, the guide member is guided in the sludge area by means of guide shoes fitted onto its blades. A stationary toothed overflow distributor is provided in the top of the container and is continuously charged with raw sludge by means of the intake connection. The guide member is driven by means of the guide member shaft end which projects from the container cover.

8 Claims, 3 Drawing Figures

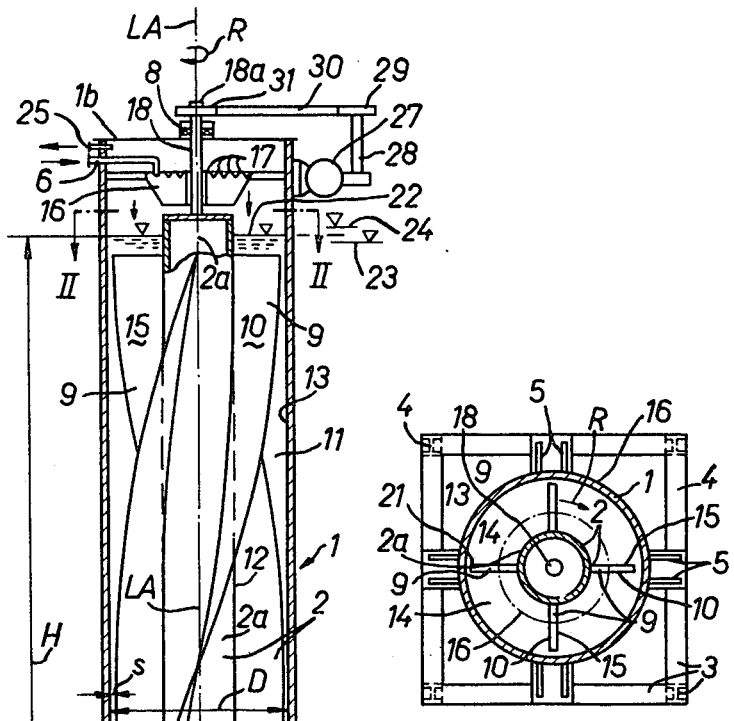
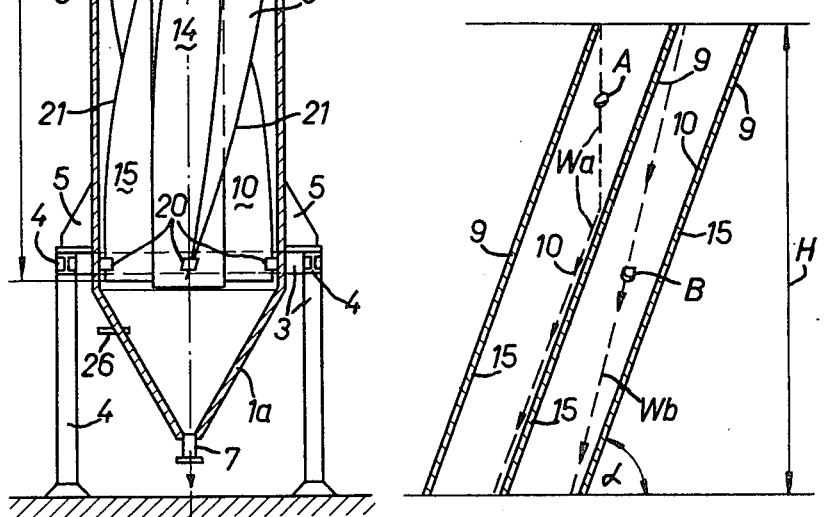
Fig 1
Fig. 2
Fig. 3

CONTAINER FOR PASTEURIZING SLUDGE

BACKGROUND OF THE INVENTION

The invention relates to a container for pasteurizing sludge, particularly sewage sludge in which the raw sludge is supplied at the necessary pasteurization temperature.

In known pasteurization systems of this type, the sludge is initially heated to the pasteurization temperature, then introduced into the pasteurization container and left to stand in the latter for approximately 30 minutes. In other known installations, the sludge is circulated through a pasteurization container and a heating station until it has reached the pasteurization temperature, after which the heated sludge is also left to stand in the pasteurization container for 30 minutes. In these known systems, the pasteurized sludge is drained off from the container at the end of the pasteurization time, when a new pasteurization cycle commences. Thus, these typical batch plants operate on a discontinuous basis.

In other known installations, attempts have been made to overcome the disadvantage of discontinuous batch operation, i.e. the batchwise or intermittent heating, pasteurization and cooling of the sludge, by providing a plurality of pasteurization containers which are charged in a time-staggered manner to obtain a quasi-continuous operation.

All of these known installations have an important disadvantage. The container in which the sludge is pasteurized is always infected at certain points and possibly everywhere, either by the infected sludge itself, or by the infected air, or by both of them, so that when the pasteurized sludge is drawn from the pasteurization container, the sludge is immediately contaminated again by the reabsorbed infected air.

BRIEF SUMMARY OF THE INVENTION

One object of the invention is to overcome the disadvantage described above and to provide a pasteurization container in which there is no infection of the container and consequently no reinfection of the pasteurized sludge.

According to the invention, this disadvantage is solved by an approximately cylindrical pasteurization container formed as a vertically standing flow container and constructed in a hydraulically slender manner with respect to its height/diameter ratio and provided with an upper inlet for the raw sludge and a lower outlet for the pasteurized sludge. A pivotally-mounted central guide member, driven by a motor and being in the shape of a geometric solid of revolution in conformance with the shape of the container is incorporated into the container coaxially with respect to the longitudinal axis thereof. The central guide member is provided with a plurality of helically-wound blades which run from top to bottom and which form helical deflectors for the sludge, and whose radial height corresponds to the circular, cylindrical space between the guide body core and the inner container wall. The cross-sectional passage of the container is subdivided by the helically-wound blades into a plurality of helically-wound individual channels extending from top to bottom thereof.

According to a preferred embodiment of the pasteurization container, the guide member is suspended outside at the top end of the container in a combined radial/axial bearing and is guided in the sludge chamber on its helical blades in the lower part of the container.

A preferred embodiment of the pasteurization container comprises plastic guide shoes fitted to the base portions of the guide member blades, and adapted to guide the guide member in the container, the shoes being made preferably from Teflon, a plastic material characterized by particularly good sliding properties and an excellent aging resistance.

According to another preferred embodiment of the pasteurization container, the container, the guide member, whose outer contour and core are constructed in a cylindrical shape, and the guide member blades have continuous helical deflectors extending from top to bottom.

According to another preferred embodiment of the pasteurization container, the guide member speed is selected in such a way that each of its individual channels is exposed to at least 4 to 5 complete charging cycles for an average sludge transit time of 45 to 50 minutes.

In another preferred embodiment of the pasteurization container, the guide member has six blades in the form of a generating helix having a pitch angle of at least approximately 70 degrees.

According to another preferred embodiment of the pasteurization container, a fixed toothed overflow distributor is provided at the upper end thereof, and the distributor is continuously charged with the raw sludge to be pasteurized by means of an intake connection arranged laterally on the top of the container.

BRIEF DESCRIPTION OF THE DRAWINGS

The objects, advantages and features of this invention will be more clearly appreciated from the following detailed description when taken in conjunction with the accompanying drawing, in which:

FIG. 1 is a cross-sectional view of one embodiment of the pasteurization container of this invention;

FIG. 2 is a horizontal cross-section of the invention along the line II—II of FIG. 1;

FIG. 3 is a partial projection of the central guide chamber of the container of FIG. 1 illustrating the different paths of sludge particles having different specific gravities.

DETAILED DESCRIPTION OF THE PREFERRED EMBODIMENT

In FIG. 1, a vertically standing, substantially cylindrical pasteurization container 1 formed as a flow container is provided with a pivotally-mounted central guide member 2, whose outer contour also has a substantially cylindrical shape and whose longitudinal axis LA coincides with the longitudinal axis of container 1. Pasteurization container 1 rests on a container base 3 which in this case is essentially assembled from I-beams 4 and to which the container 1 is secured by means of lateral brackets 5 (See also FIG. 2). At its top, container 1 is provided with a lateral intake connection 6 for the continuous charging thereof with mechanically, coarsely crushed raw sludge, already heated to the necessary pasteurization temperature of, for example, 70° C. At its bottom on its conical base 1a, container 1 is provided with a central outlet connection 7 for the continuous draining of the pasteurized sludge by means of a sludge pump not shown in FIG. 1.

At the upper end of container 1, the central guide member 2 is suspended in a combined radial/axial bearing 8 disposed on the upper cover plate 1b of the container. Guide member 2 is provided with four relatively thin-walled wound blades 9, which are arranged continuously from top to bottom on a cylindrical core 2a of guide member 2 in much the same way as a multiple thread assembly screw and, as in this case, a right-hand assembly screw. Blades 9 have four helical deflectors 10 which face frontally, relative to the direction of rotation R thereof. Blades 9 have a uniform cross-sectional spacing about core 2a. The height of the four rib-like, helically-wound blades 9 radially measured in the horizontal plane, when account is taken of the necessary clearance S between container 1 and rotary guide member 2, corresponds to the radial width of the circular cylindrical space 11 between the circumferential surface 12 of guide member core 2a and the container wall 13, so that the circular cross-section of the passage of cylindrical container 1 is subdivided by the four blades 9 of guide member 2 into four continuous helically-wound individual channels 14 extending from the top to the bottom of container 1. Each channel 14 has the same cross-sectional shape and the same cross-sectional dimension. Channels 14 are bounded radially by front deflectors 10 and rear helical surfaces 15 of the four blades 9 (See also FIG. 2.). As can be seen from FIG. 1, when viewed from the top, as in FIG. 2, the deflectors 10 of the helical blades 9 are oriented as a right hand screw. Also from these figures it is clear that the direction of rotation of the guide member and the blades is clockwise so that there is an upward component angle of the deflector, the effect of which on the sludge is accentuated when guide member 2 is rotated. Of course the rotation direction and helical pitch direction could both be opposite to that shown.

The upper end of container 1 is provided with a bowl-shaped toothed overflow distributor 16 secured in a detachable manner to the container so that it is stationary with respect to the container The distributor 16 is continuously filled with the incoming raw sludge via lateral intake connections 6, so that the sludge which flows over edge 17 is continuously distributed into the four individual channels 14. Guide member 2 is supported by a vertical shaft 18 guided by bearing 8. Shaft 18 passes through the center of the annularly-shaped toothed overflow distributor 16 in spaced relation thereto and is rigidly connected to container 1.

In the lower part of container 1, guide member 2 is held in place and provided with adequate clearance between surface 21 and wall 13 by guide shoes 20 which are attached to guide member blades 9 and which project somewhat beyond the narrow outer peripheral surface 21 thereof. Guide shoes 20 are preferably made from the plastic material Teflon, a registered trademark for polytetrafluoroethylene, since it has excellent sliding properties and a good resistance to aging.

The discharged pasteurized sludge is continuously drawn off through the lower outlet connection 7 of container 1. The discharge of pasteurized sludge is continuously controlled by permanently monitoring the average sludge level 22 in container 1 to keep the amount of discharged sludge equal to the quantity of raw sludge fed in through the upper intake connections 6 so that the average sludge level 22 is maintained between a lower limit 23 and an upper limit 24. This produces a transit time t for the sludge in pasteurization container 1 which can be set at a constant value.

Container 1, which is provided at its upper end with an air vent 25, has on its conical base 1a a temperature measuring connection 26 which constantly monitors the temperature of the pasteurized sludge discharged from the container. The desired temperature, for example 70° C., of the sludge as it enters the pasteurization container through the intake connection 6 can consequently be maintained in a sufficiently accurate manner, after being preheated by the actual pasteurized sludge, either by the controlled supply of steam to the sludge or by regulated heating of the sludge in a heat exchanger by hot water. The temperature loss of the sludge through the pasteurization container 1 can be taken into consideration in establishing the desired value for the sludge intake temperature in such a way that when the sludge leaves the container through the outlet connection 7, the sludge still has a temperature of 70° C. For this purpose, the sludge heating is regulated by means of a temperature sensor incorporated into measuring connection 25 for determining the pasteurized sludge discharge temperature so that the raw sludge entering container 1 via intake connections 6 has a temperature which exceeds 70° C. by the amount of the temperature loss in the container.

FIG. 2, which is a cross-sectional view of the pasteurization container 1 of FIG. 1, clearly shows the four helically-wound individual channels 14 with a circular cross-section having quadrants radially bounded by the four relatively thin-walled blades 9 of the central guide member 2. It also shows the helical deflectors 10 formed by blades 9 and which face in a frontal direction with respect to the direction of rotation R of guide member 2. FIG. 2 also shows the rear helical surfaces 15 of the guide member, the central axis of the guide member shaft 18 which is coincident with the container axis, the tube-like cylindrical guide member core 2a away from which the four blades 9 project radially, the toothed overflow distributor 16, as well as the container stand 3 formed from the I-beam steel sections 4 and the four pairs of brackets 5 which secure the cylindrical pasteurization container 1 to the stand 3.

The operation of the pasteurization tank with reference to FIGS. 1 and 2 will now be described in further detail by describing the technical considerations essential for sludge pasteurization.

It is desirable to obtain a flow rate in container 1 which is as uniform as possible across the container cross-section, i.e. the so-called "piston flow" in which all the sludge particles pass through the cylindrical pasteurization container 1 at an identical speed in much the same way as they would with a piston. To obtain such a flow rate, container 1, which is already very slender with respect to its height, is made much more slender by the previously described addition of the central guide 2 so that the effective slenderness ratio $\lambda = H/D$, where H is the container height through which sludge actually flows, for example 7.0 m, and D is the container diameter, for example 1.5 m, falls approximately in the range of from 7.5 to 10. In addition, the use of the central guide member in container 1 prevents a break in the center of the container which could considerably impair the pasteurization process.

Irregularities in the sludge flow which could occur as a result of different specific gravities of the individual sludge portions are prevented by fixing the average transit time t of the sludge at between 45 to 50 minutes instead of only 30 minutes as is normally the case. If the liquid is made completely homogeneous, it is possible to ensure that the transit time be $t > 30$ minutes in all cases. However, even pulverized sludge is never completely homogeneous. Although the mechanical sludge preparation, i.e. the crushing of the raw sludge before it enters the pasteurization container 1, which is done to homogenize the sludge, ensures that no compact lumps of sludge are introduced into the container, the sewage sludge still contains sands and sometimes even other heavy particles. Even with a completely uniform sludge speed, these particles drop more rapidly than other sludge particles due to their higher specific gravity ($g/cm^3$) and may therefore arrive at the container outlet 7 (See FIG. 1.) after only a transit time of $t < 30$ minutes. This would be prejudicial to the desired pasteurization effect.

In order to negate the influence of the different specific gravities of the individual sludge portions and consequently their different speeds of fall, besides adding the central guide members to increase the slenderness ratio, continuous helical surfaces 10 and 15 passing from top to bottom are provided on guide member 2, as previously described. The number of the surfaces or the rib-like blades 9 on guide member 2 which form them, together with the pitch of the surfaces (See FIG. 3.) for a given effective height H of container 1 is determined, as shown in FIG. 3, by the predetermined minimum value of the transit time t, for example 30 minutes. Even a very heavy particle A which has a rapid vertical fall and which follows a short path Wa and subsequently slides on the frontal helical deflector 10 of the following blade 9 with the average sludge speed must have a transit time which is not less than t. For a particle B, which takes the path Wb, its transit time must not exceed t (See FIG. 3.).

All these conditions, which are only diagrammatically represented in FIG. 3, can be fulfilled by having a predetermined effective container height H of 7 m and by having six helically-wound blades 9 arranged in a regular circularly-divided pattern and/or six frontal helical deflectors 10 having six helically-wound individual channels 14 with a pitch angle $\alpha = 70°$ of the helix producing the channels as measured at the outer guide member diameter. This configuration ensures that even the heavy particles contained in the sludge are subject to the necessary minimum transit time t of 30 minutes. For reasons of clarity, in the embodiment of FIGS. 1 and 2, guide member 2 is shown only with four blades, but in the preferred embodiment, six-bladed guide members are used.

In dividing the sludge flow into the individual helical channels 14 of guide member 2, it is assumed that each of the channels is charged with the same quantity of sludge. This can be facilitated by incorporating into the container 1 a toothed overflow distributor 16, but can certainly never be achieved only by such a device. To assist the toothed overflow distributor 16 in achieving such a result, guide member 2, together with its helical deflectors 10 and 15, is rotated slowly, e.g. at approximately six revolutions per hour. As a result, each channel 14 is exposed to roughly 4.5 to 5 complete charging cycles during the average sludge transit time t of, for example, 45 to 50 minutes, which ensures that all of the channels are charged with the same quantity of sludge. The rotary guide member 2 is driven by means of an electric motor 27 and a reduction gear coupled to the shaft end 18a (See FIG. 1.) which projects upwardly out of the container cover 1b. The reduction gear is constructed in accordance with the desired speed of rotation of guide member 2 and may be a worm drive whose output shaft 28 in this case acts on guide member shaft 18 via a chain wheel 29, a chain 30 and a chain wheel 31.

A very important consideration which is determinative of the value of any pasteurization system is the certainty with which it is possible to prevent a reinfection of the already pasteurized sludge in the system.

In the case of the pasteurization container 1 constructed as explained in detail relative to FIGS. 1 to 3, a clearly defined pasteurization state is associated with each point in the container. Along the sludge path to a particular end point, there is still partly unpasteurized sludge in a transition state, while at a particular end point of this path there exists only pasteurized sludge.

In contrast, in the known, discontinuous batch-wise operation, for example in the known multi-chamber pasteurization container, at one and the same point in the container, pasteurized and unpasteurized sludge is alternately present, according to the status of the successive charging cycles.

With respect to the different sludge states of the pasteurization container 1 of FIGS. 1 and 2, it can be seen that the upper end of the container 1 always constitutes a dirty area having unpasteurized sludge, while the lower container end constitutes a permanently clean area having pasteurized sludge. Thus, at the upper end of the container, it does not matter if new germs are continuously introduced into the sludge through the air or through back-flowing condensate from the vent line (See air vent 25 in FIG. 1.) or from any other point at the top of the container. However, at the lower end of the container, i.e. in the clean area, reinfection of the pasteurized sludge is no longer possible. This area is sealed to everything except the sludge. The sludge, which arrives at the lower end, has already passed through the pasteurization container 1 and is therefore pasteurized when it reaches this area. If the cooling and the transportation to the digestion tank of the pasteurized sludge takes place in absolutely tightly sealed pipelines, it is certain that the purpose of pasteurization, i.e. the introduction of completely pasteurized sludge into the digestion tank, is effectively achieved.

Apart from this important advantage of reliably avoiding any reinfection, the pasteurization container described above also has the advantage of being completely continuously operated. Compared with the above-mentioned known multi-chamber dwell tanks with time-staggered charging of the various chambers thereof, this invention provides advantages not only with regard to the apparatus required for the synchronized switching of the individual pasteurization chambers to the different successive process cycles, but also with regard to the high operating costs incurred with the prior art equipment.

In view of the above description, it is likely that modifications and improvements will occur to those skilled in the art which are within the scope of this invention.

What is claimed is:

1. An apparatus for pasteurizing sludge, comprising:
a substantially cylindrical pasteurization container adapted for conducting a longitudinal flow of sludge through a passage thereof from an upper longitudinal end to a lower longitudinal end, said container having a longitudinal dimension from said upper end to said lower end which is greater than the transverse dimension of the diameter thereof and having a longitudinal axis disposed at a transverse center thereof and extending longitudinally from said upper end to said lower end;

an upper inlet disposed at said upper end of said pasteurization container and adapted to conduct sludge into said pasteurization container;

a lower outlet disposed at said lower end of said pasteurization container and adapted to discharge treated sludge from said pasteurization container;

means for supplying sludge to said upper inlet at a predetermined pasteurization temperature;

a central guide member rotatably disposed within said pasteurization container substantially along said axis thereof, said guide member having the shape of a geometric solid of revolution and having an axis of rotation coincident with said container axis;

motor means for rotating said guide member in a predetermined direction about said guide member axis; and a plurality of helical blades wound around said guide member and secured thereto, said blades extending from said upper end to said lower end to divide said passage into a plurality of individual helical channels coextensive in length with said blades, said blades forming deflectors for said sludge, said blades having a radial dimension substantially equal to the transverse distance from said guide member to an inner wall of said passage; the pitch direction of said helical blades from said inlet to said outlet being the same as said direction of rotation.

2. The apparatus for pasteurizing sludge according to claim 1 further comprising:

radial/axial bearing means adapted for suspending said guide member adjacent said upper end and disposed outside of said chamber; and means for guiding said blades and said guide member within said chamber, said guiding means being disposed adjacent said lower end.

3. The apparatus for pasteurizing sludge according to claim 2 wherein said guiding means comprises guide shoes attached to a base of said blades adjacent said lower end, said guide shoes being formed of a plastic material.

4. An apparatus for pasteurizing sludge according to claim 3 wherein the guide shoes are made of polytetrafluoroethylene.

5. An apparatus for pasteurizing sludge according to claim 1 wherein said container, said guide member and the outer contour of said helical blades each are formed in the shape of a right circular cylinder.

6. An apparatus for pasteurizing sludge according to claim 1 wherein said guide member has a speed of rotation selected so that each of said individual helical channels is exposed to between four and five complete changing cycles for a transit time for sludge from said upper end to said lower end of said container of between 45 and 50 minutes.

7. An apparatus for pasteurizing sludge according to claim 1 wherein said plurality of helical blades comprises six blades and wherein each of said helical blades has a pitch angle of at least 70° with respect to said longitudinal axis of said container.

8. An apparatus for pasteurizing sludge according to claim 1 further comprising an overflow distributor having fixed teeth and being disposed adjacent said upper end of said container, said overflow distributor being continuously charged with raw sludge to be pasteurized by means of an intake connection transversely disposed adjacent said upper end of said container.

* * * * *